United States Patent [19]

Lin et al.

[11] 4,186,082

[45] Jan. 29, 1980

[54] HYDROCARBON PROCESS FOR INCREASING THE CONCENTRATION OF NORMAL CIS OLEFINS

[75] Inventors: Chi-Hung Lin, Wheaton, Ill.; William F. Pansing, deceased, late of Munster, Ind., by Evelyn Pansing Boyle, legal representative

[73] Assignee: Standard Oil Company (Indiana), Chicago, Ill.

[21] Appl. No.: 881,556

[22] Filed: Feb. 27, 1978

[51] Int. Cl.$^2$ .......................... C07C 7/13; C10G 25/04
[52] U.S. Cl. .................................. 208/310 Z; 585/820
[58] Field of Search ............ 208/310 Z; 260/676 MS, 260/677 AD

[56] References Cited

U.S. PATENT DOCUMENTS

| | | | |
|---|---|---|---|
| 2,866,835 | 12/1958 | Kimberlin et al. | 260/676 MS |
| 3,061,654 | 10/1962 | Gensheimer et al. | 260/677 AD |

Primary Examiner—Herbert Levine
Attorney, Agent, or Firm—William C. Clarke; Arthur G. Gilkes; William T. McClain

[57] ABSTRACT

Process for increasing the concentration of normal cis olefins in a hydrocarbon composition with pre-treated molecular sieves which have been heated to a temperature of from 400° to 500° F. for a period of about 1 to 6 hours to reach the water-zeolite equilibrium at said temperature range in the presence of water.

8 Claims, 1 Drawing Figure

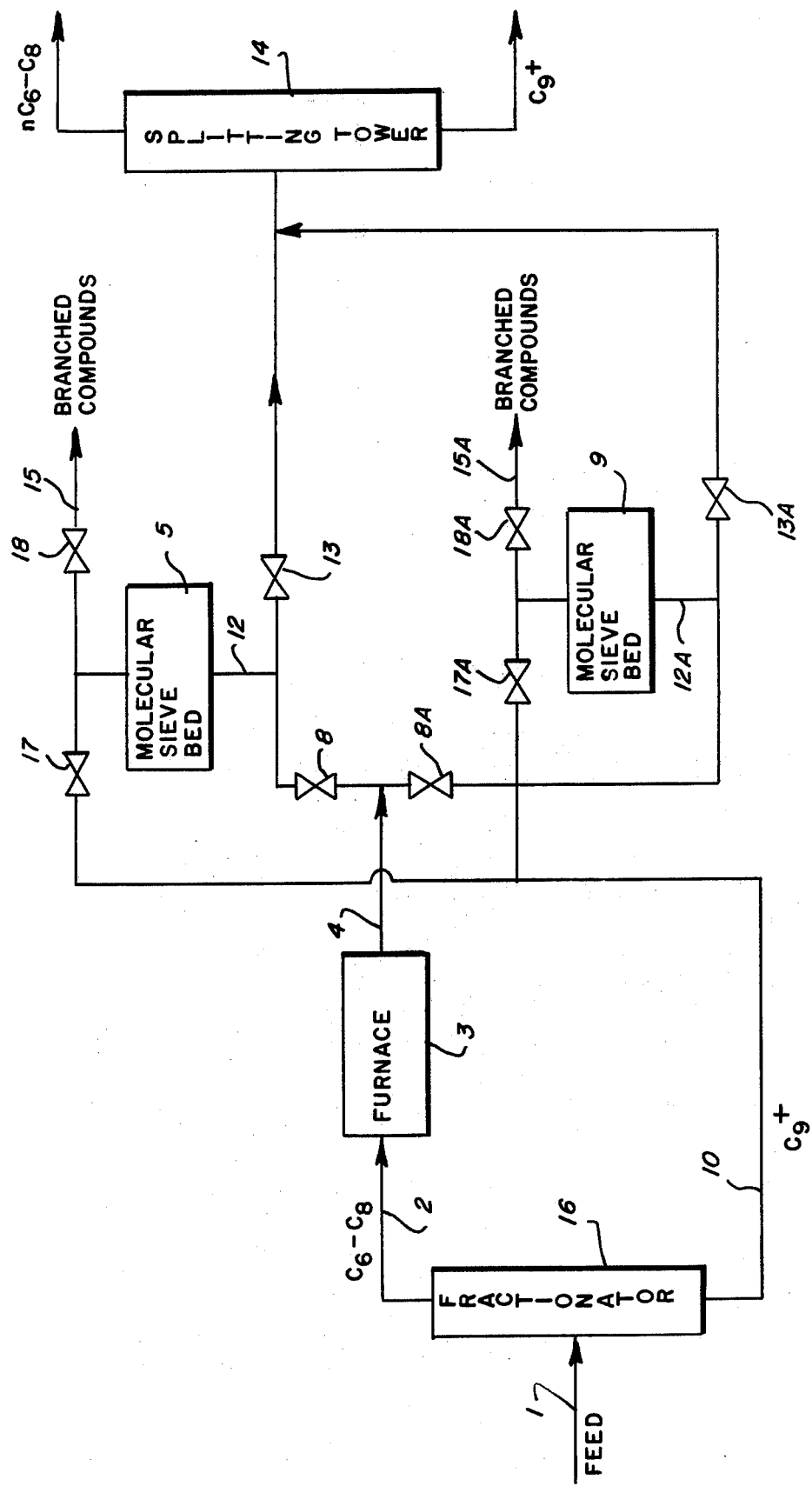

HYDROCARBON PROCESS FOR INCREASING THE CONCENTRATION OF NORMAL CIS OLEFINS

BACKGROUND OF THE INVENTION

This invention relates to a concentration process wherein normal cis olefins are concentrated in a hydrocarbon composition.

It is well-known that normal olefins have desirable properties over branched olefins as excellent starting materials for linear plasticizer alchols. These alcohols exhibit better low temperature properties than non-linear plasticizer alcohols and also increased bio-degradability. Separation of normal olefins from branched olefins is accordingly exceedingly desirable.

It is well-known also that certain natural and synthetic zeolites have the property of preferentially absorbing certain types of hydrocarbons. These zeolites, known as molecular sieves, have crystalline structures containing a large number of pores of uniform size. In different zeolites, these pores can vary from 4 Angstroms (A°) to 15 A° or more in diameter but in any one zeolite the pores will be of substantially uniform size. Specific zeolites which are referred to as molecular sieves accordingly can be utilized for separating specific hydrocarbons on the basis of the size and shape of the adsorbate molecule. These molecular sieves have a sorption area available on the inside of the uniformly sized pores. With such an arrangement molecules of a certain size and shape enter the pores and are adsorbed while larger or differently shaped molecules are excluded.

It is known that molecular sieve type 5A is capable of separating straight chain hydrocarbons from non-straight chain hydrocarbons by the acceptance-exclusion principle based on molecular size. Many processes based upon this have been successfully applied for separations of paraffinic hydrocarbon mixtures. However, because the acceptance-exclusion principle operates based on molecular size, the efficiency of separating branched olefins from normal olefins has suffered because of the difficulty of separating the cis isomer configuration from branched olefins.

The cis isomer of normal olefins in molecular configuration is more akin to branched olefins than to the trans isomer of normal olefins. Accordingly, separation of the cis isomer from branched olefins using molecular sieve techniques in the prior art has not been as complete as has been the separation of the trans isomers from branched olefins.

The molecular sieve effect whereby cis isomers are adsorbed less readily by synthetic zeolites of the CaA type has been reported and is generally known, (Petryaeva et al., Izu. Akad. Nauk SSSR, Ser. Khim. 1967(8), 1860-2, CA 6640j (1968)), although the NaX zeolites indicate an adsorption of all hexenes equally well, linear and non-linear.

U.S. Pat. No. 2,866,835 to Kimberlin et al. relates to a process for separating olefins from hydrocarbon streams using molecular sieves with pore diameters of about 4.5 to 5.5 Angstrom (A°) units. Kimberlin taught that cis olefins in the original stream were not significantly adsorbed by the sieve and that the sieve adsorbate olefins were substantially completely of the trans type. The cis olefins were not preferentially separated from the hydrocarbon stream by being adsorbed by the molecular sieve.

U.S. Pat. No. 2,988,578 to Fleck et al. relates to a process for the isomerization of hydrocarbons and the separation of the cis-trans isomers by use of a 5 Å molecular sieve. The mixed isomerized olefins are preferentially adsorbed to result in a substantially higher trans content over the cis content rather than a racemic mixture.

U.S. Pat. No. 2,850,549 discloses the separation of cis and trans olefin isomers wherein the separation is carried out over a long period of time, e.g., 24 hours.

U.S. Pat. No. 3,524,895 discloses a method for the separation of cis and trans hydrocarbon isomers which is achieved by passing a mixture thereof through a crystalline aluminosilicate adsorption zone for a relatively short adsorption period. It has been found that cis isomers have a substantially lower adsorption rate than do trans isomers and that therefore trans isomers can be separated thereby.

The lesser adsorption of the cis isomer by synthetic zeolites results in a loss of substantial quantities of the cis isomer in that cis isomer is not separated from the hydrocarbon stream as well as is the trans isomer. A method has been found whereby the cis isomer can be recovered in good yield from branched olefins. Overall concentration of cis and trans isomers is improved over the concentration obtained of cis-trans isomers from the hydrocarbon stream without use of the method of the instant invention.

SUMMARY OF THE INVENTION

Process for concentrating cis isomers of normal olefins in a hydrocarbon stream with molecular sieves which have been pre-treated by heating to a temperature of from 400° to 500° F. for a period of about 1 to 6 hours.

DETAILED DESCRIPTION OF THE INVENTION

Feedstocks which can be used in the process of this invention include mixtures of normal and branched olefins, normal and branched paraffins and aromatic hydrocarbons having from about 4 to about 20 carbon atoms per molecule, preferably from about 4 to about 10 carbon atoms per molecule, most preferably from about 6 to about 9 carbon atoms per molecule.

Specifically, feedstock components can contain mixtures of 2,2-dimethylbutane; 2,3-dimethylbutane; 2-methylpentane; 3-methylpentane; normal hexane; normal pentane; iso-pentane; 2,2-dimethylpentane; 2,3-dimethylpentane; 2,4-dimethylpentene-1; 2,4-dimethylpentene-2; 5-methyltrans-hexene-2; 5-methyl-cis-hexene-2; heptene-1; heptene-3; transheptene-2; cis-heptene 2; etc. Higher molecular weight feedstocks can be utilized and it is not considered necessary to specifically name all the components possible in the above general group. The terms "branched paraffins" and "branched olefins" when used to define components of the feedstock shall mean any paraffin or any olefinic material having a alkyl substitution of a carbon atom or atoms on the paraffin or olefin chain to render a non-normal or iso-compound. Specifically, branched paraffins and branched olefins include those paraffins and olefins having more than one or more alkyl substitutions on the normal chain. Spefically, a single methyl or higher alkyl group is substituted on the chain to form a non-normal configuration. The terms "normal paraffins"

and "normal olefins" are self-explanatory and includes those paraffins and olefins which are essentially straight chain paraffins and olefins. The feedstock can contain small quantities of other hydrocarbon types such as aromatic materials, iso-paraffins, iso-olefins and cyclo hydrocarbons such as cycloparaffins and cyclo-olefins. Other contaminants such as organic nitrogen and sulfur compounds can be included within the general term of the feedstock. It is, however, preferred to reduce any of the contaminants in the feedstock to a minimum in order to eliminate adverse effects on the separation caused by such contamination of the adsorbent and to reduce any possibility of such reactions such as isomerization and polymerization from occurring. Desulfurization of the feedstock in a liquid phase process is preferred to a frequent regeneration of the adsorbent material. Frequent regeneration is preferred in a vapor-phase process in preference to desulfurization of the feedstock.

In some instances where the feedstock contains components covering a 3 to 6 or higher carbon number spread some of the higher molecular weight singly-branched paraffins and olefins may equally compete with lower molecular weight multi-branched paraffins and olefins. To prevent interference of this type, it is preferable to reduce the boiling range of the feedstock to less than a 3-carbon number spread.

Specific suitable hydrocarbon feedstocks include catalytic naphthas and coker naphthas. A typical feedstock is a 190°-310° F. heavy catalytic naphtha fraction composed of $C_4$ to $C_{12}+$ olefins with an API gravity of 57.4 at 60° F. and containing $C_7$–$C_9$ linear olefins. A coker naphtha is defined as a hydrocarbon product stream from a coker wherein the product stream has a boiling point within the range of from about 60° to 420° F. at atmospheric pressure. In the operation of the process of the instant invention, the total $C_4$ to $C_{12}+$ catalytic naphtha or coker naphtha is fractionated to obtain a desired three to four-carbon normal olefin feed such as a $C_7$ to $C_9$ or a $C_6$ to $C_{10}$ normal olefin feed.

All the known molecular sieves can be treated and used in accordance with the invention. For example, the molecular sieves of A type sold by Linde Company, Division of Union Carbide Corporation, can be treated.

In the case of concentration of cis isomers of $C_7$–$C_8$ olefins, molecular sieves are employed the pore diameter of which is between the size of the said cis isomer and that of the 1-normal olefin of the $C_7$–$C_8$ olefin. In the case of concentration of cis isomers of $C_7$–$C_8$ olefins, a sieve of type 5A is used, that is to say a sieve whose pore diameter is from about 4.5 to 5.5 Å. It is to be understood that the expression "pore size" as used herein refers to the apparent pore size, as distinguished from the effective pore diameter. The apparent pore size can be defined as the maximum critical dimension of the molecular species which is adsorbed by the zeolite molecular sieve in question under normal conditions. Maximum critical dimensions can be defined as the diameter of the smallest cylinder which will accommodate a model of the molecule constructed using the best available values of bond distances, bond angles and Van der Waal radii. Effective pore diameter is defined as the free diameter of appropriate silicate ring in the zeolite structure. The apparent pore size for a given zeolite molecular sieve will normally be longer than the effective pore diameter.

The term "zeolite" in general refers to a group of naturally occurring and synthetic hydrated metal alumina-silicates, many of which are crystalline in structure. There are, however, significant differences between the various synthetic and natural materials in chemical composition, crystal structure and physical properties such as X-ray powder diffraction patterns.

Synthetic zeolite type A in its calcium cation exchanged form known as zeolite 5A is the preferred molecular sieve. Other useful zeolites of natural or synthetic origin having pore sizes of about 5 Angstroms include chabazite, mordenite, gmelinite, erionate and those known as types D, R, S and T.

The structure of crystalline zeolite A molecular sieves can be described as an open three-dimensional framework of $SiO_4$ and $AlO_4$ tetrahedra. The tetrahedra are cross-linked by the sharing of oxygen atoms, so that the ratio of oxygen atoms to the total of the aluminum and silican atoms is equal to two, or $O/(Al+Si)=2$. The zeolites are activated by driving off substantial quantities of the water of hydration that is present and the space which remains in the crystals after activation is available for adsorption of molecules that have the size, shape and energy which permits their entry into the pores of the molecular sieves.

It is theorized without being bound by such theory that the instant invented process operates by controlling the amount of water present in the zeolite molecular sieves. A given range of water in the zeolite sieves wherein the water content is at equilibrium within the temperature range of from about 400° F. to about 500° F. is theorized as being required for the operation of this process. Accordingly, the zeolite molecular sieve bed is prepared by heating the bed to a temperature within the range of 400° to 500° F. to drive off excess water if adsorbed water content is greater than is required for the process or by heating the bed in the presence of water vapor at a temperature of 400° to 500° F. for 1 to 6 hours if adsorbed water content is less than at equilibrium stage within the temperature range of 400°–500° F. According the term "water-zeolite equilibrium" is defined as that concentration of water normally present in a zeolite composition within a specific temperature range and in the presence of a source of water.

Patent literature contains numerous references to the activation of zeolites for use. It has been reported, U.S. Pat. No. 2,866,835, that the capacity of molecular sieves to separate cis-trans and trans-n olefins from n-paraffins is greatly reduced if water is present even in small quantities since it is more strongly adsorbed than most hydrocarbons. The conventional means of dehydration is accomplished by purging with relatively dry gas at temperatures of about 500° to 800° F. U.S. Pat. No. 3,706,813 teaches use of zeolites for separation of multi-branched paraffins after the zeolite has been contacted in a muffle furnace at temperatures of about 500° C. for a time sufficient to drive volatile materials and to reach a constant weight with water content within a range of from 3 to 8 wt. percent. U.S. Pat. No. 3,331,882 teaches contacting zeolite with steam at temperatures ranging from 800° to 1600° F. for time periods ranging from five minutes to about four hours. After the steam pretreatment, excess moisture is removed by heating the zeolite at temperatures of from about 700° to about 1000° F. while flowing a dry, inert gas until the water content in the off gas reaches an acceptable level, anywhere from less than 0.1 to essentially 0.0 percent by weight.

Accordingly, it is indeed surprisingly that a pretreatment of molecular sieves of less than 500° F., and preferably at a temperature within the range from about 400° to about 500° F. provides a molecular sieve with a high degree of separation of cis isomers of hydrocarbons having from four to twenty carbon atoms. Also, it has been found that regeneration by the conventional methods of steaming, heating, evacuation and the like at temperatures over 500° F. result in a marked decline in the separation capacity of the zeolite as regards the aforesaid cis isomers. For example, the pretreatment of molecular sieves at 700° F. gave a separation factor for cis-heptene-2 over 5-methyl-hexene-2 of only 3.7 although the overall normal over branched separation factor was as high as 31.

Sulfur compounds tend to be preferentially adsorbed on molecular sieves and reduce their adsorption capacity. Consequently, either desulfurization of a sulfur-containing feed or frequent regeneration of the adsorbent is required. A vapor phase process can incorporate a frequent regeneration step using available technology.

Typically in the concentration process of this invention the feedstock is heated to a suitable temperature and then transferred to a fractionating zone wherein the boiling range of the feedstock is reduced to a 3-carbon number spread.

Process conditions within the molecular sieve bed can be either gas or liquid phase at a temperature within the range from about 100° F. to about 500° F., and any suitable pressure from atmospheric to about 1500 psig. with typical feed pressures ranging between about 50 and 600 psig. Flow rates are within the range of 0.1 to 5 V/V/hour. Temperatures should be as high as possible consistent with type of feed and whether gas phase or liquid phase.

If temperature below 100° F. are used, liquid phases of otherwise gaseous feedstocks may be encountered and the rate of adsorption is lower than economically desirable. If temperatures above 500° F. are employed, the zeolite molecular sieve bed is deactivated and the concentration of the cis isomer is unsatisfactory. Subatmospheric pressures engender the problems of vacuum techniques with possibilities of air leaks into the system. Also, mass flow rates involve excessive velocities. Above 1500 psig., special equipment is required and feed hold-up in the bed voids becomes unreasonably high.

Depending upon carbon chain length, either a gas phase or a liquid phase process can be used. With carbon chain lengths of $C_4$ to $C_9$, a gas phase process is preferred because the mass transfer rate and rate of adsorption is higher than with a liquid phase process. Conditions of operation in a gas phase process are typically within the range of about 300° F. to about 500° F. at a pressure of from atmospheric to 500 psig.

With carbon chain lengths of from about $C_{10}$ to $C_{20}$, a liquid phase process is preferred as being more economical than a gas phase pressure. An uneconomical heat input is required to vaporize hydrocarbons of $C_{10}$ to $C_{20}$ chain length as compared with the temperature and pressure required to maintain the feedstock in the liquid phase.

Since zeolite molecular sieves are typically acidic, the zeolite sieves can act as polymerization catalysts, promoting polymerization of the feed molecules. Additionally, cracking of the hydrocarbon feedstock can occur with formation of coke and lighter materials. The resulting plugging of the molecular sieve bed due to polymerization of the feed and coke formation reduces adsorption rate and the yield drops.

Regeneration of the molecular sieve bed is achieved by increasing the bed temperature sufficiently to perhaps 1000° F. in the presence of a controlled amount of oxygen in nitrogen to burn off the polymers and coke formed on the molecular sieves. The bed is cooled with nitrogen and water vapor at a temperature within the range of 200° to 400° F. for 1 to 6 hours, or as necessary, at a temperature of 400° to 500° F. wherein the water content of the molecular sieve bed is at a point of stable equilibrium. The bed is then ready for use.

Stripping the adsorbed normal cis-trans olefins from the bed can be performed with any suitable relatively inert gas or liquid. Suitable stripping gases are nitrogen, argon, lower molecular weight saturated hydrocarbons or any branched gaseous hydrocarbon which has a different boiling point. A stripping temperature within the range of 400° to 500° F. is preferable. Flow rate of the stripping gas can be as much as five times that of the feedstock.

In the embodiment of this invention, a gas phase or liquid phase operation can be used although gas phase operation is preferred because of sulfur deactivation, molecular sieve regeneration, interstitial loading, process flexibility and mass transfer rate.

In summary, the instant process comprises a method for increasing the concentration of normal cis-olefins in a hydrocarbon composition, which comprises passing a hydrocarbon composition comprising normal cis-olefins containing from about 4 to 20 carbon atoms and at least one member selected from the group consisting of branched olefins containing from about 4 to 20 carbon atoms, normal and branched paraffins containing from about 4 to 20 carbon atoms and aromatic hydrocarbons into a pretreated molecular sieve adsorption zone or bed, withdrawing unadsorbed hydrocarbons and recovering adsorbed hydrocarbons wherein said molecular sieve has been pretreated at a temperature within the range of from about 400° to about 500° F. for a period of 1 to 6 hours to reach a water-zeolite equilibrium.

Embodiments of the process of the present invention may be found in the following examples. These embodiments and examples are presented for purposes of illustration only and are not intended to limit the scope of the invention.

Process Description

A specific embodiment of the process of the present invention is presented in the FIGURE. Auxiliary equipment, such as pumps and heat exchangers, is not shown in the drawing. Such auxiliary equipment is well-known to those skilled in the art and the uses and locations of this equipment in this particular process system will be recognized easily by those having ordinary skill in the art.

Fresh feedstock comprising normal olefins, branched olefins, aromatics and possibly some normal and branched paraffins is introduced into the process by line 1 into a fractionator 16 wherein it is fractionated into a light overhead of $C_6$-$C_8$ fraction and a heavy bottom of $C_9+$ which is withdrawn through line 10. The overhead fraction is withdrawn through line 2 and is charged through furnace 3 from where it is passed through line 4 through molecular sieve bed 5. Valves 8A and 17 are closed while valves 8 and 18 are opened. Branched compounds (isoparaffins, aromatics, iso-olefins) are removed through line 15. Molecular sieve bed 5 is a bed of Linde Sieve Type 5A. This sieve material has a pore size of about 5 A° and has been pretreated at a temperature of 400°-500° F. for a period of approximately 4 hours.

After operation in the above described method for a brief processing period, i.e., whereby sufficient adsorption of cis-trans isomers and the other normal olefins takes place within the molecular sieve beds, switch valve 8 and switch valve 8A are turned. Valves 17 and 13 are opened and valves 8 and 18 are closed. The overhead in line 4 is diverted to molecular sieve bed 9 and the bottoms fraction from line 10 is diverted to the top of molecular sieve bed 5. The overhead passes through bed 5 and the $C_9+$s strip the previously adsorbed $C_6$–$C_8$ cis-trans isomers from the bed, carry them through line 12 through switch valve 13 to splitting tower 14. In splitting tower 14, the feed is split between cis-trans $C_6$–$C_8$ and $C_9+$ bottoms. Again, after operation in the above described method for a brief processing period, the cycles are reversed.

EXAMPLE I

Equilibrium adsorption studies were carried out in liquid and zeolite mixtures at room temperature. A hydrocarbon mixture containing normal olefins of known composition was contacted with pretreated Linde 5A molecular sieves and the raffinate, after equilibrium was reached, in approximately 20 hours, was collected and analyzed by gas chromatography. A non-adsorbable component, 2,4-dimethyl pentane, was added to the hydrocarbon mixture to serve as a dummy component in the calculation. The molecular sieves were pretreated at 450° F. for 4½ hours. Resulting data are in Table I.

TABLE I

| | |
|---|---|
| Pretreatment temperature of 5A molecular sieves | 450° F. |
| Experimental temperature | 81° F. |
| Adsorbent charged | 7.934 grams |
| Feed charged | 4.040 grams |

Composition of liquids, grams/gram of 2,4 dimethylpentane

| | Feed | Adsorbed | Raffinate |
|---|---|---|---|
| 2,4-dimethylpentane | 1.0 | | 1.0 |
| 2,4-dimethylpentene-1 | 0.479 | 0.019 | 0.460 |
| 2,4-dimethylpentene-2 | | | |
| 2-methylhexene-1 | 0.511 | 0.015 | 0.496 |
| 2-methylhexene-2 | | | |
| trans heptene-2 | 0.673 | 0.447 | 0.226 |
| cis heptene-2 | 0.402 | 0.105 | 0.297 |

*Separation factors:
Normal over branched olefins: 30
cis-heptene-2 over 2-methylhexenes: 12
*Separation factor is defined as:

$$\frac{\text{Weight Fraction of Component 1}}{\text{Weight Fraction of Component 2}} \text{ in adsorbed phase} \times \frac{\text{Weight Fraction of Component 2}}{\text{Weight Fraction of Component 1}} \text{ in raffinate}$$

wherein Component 1 is total normal components and Component 2 is total branched components

EXAMPLE II

The conditions of Examle I were repeated except that the pretreatment temperature of the 5A molecular sieves was 700° F. The results are in Table II.

TABLE II

| | |
|---|---|
| Pretreatment temperature of 5A molecular sieves | 700° F. |
| Experimental temperature | 79° F. |
| Adsorbent charged | 7.188 grams |
| Feed charged | 3.555 grams |

Composition of liquid, gram/gram of 2,4-dimethylpentane

| | Feed | Adsorbed | Raffinate |
|---|---|---|---|
| 2,4 dimethylpentane | 1.0 | | 1.0 |
| 2,4 dimethylpentene-1 | 0.416 | | 0.053 |
| 2,4-dimethylpentene-2 | | | 0.341 |
| trans-5-methylhexene-2 | 0.155 | 0.007 | 0.148 |
| cis, 5-methylhexene-2 | 0.423 | — | 0.426 |
| heptene-1 | 0.549 | 0.283 | 0.266 |
| heptene-3 | 0.561 | 0.272 | 0.289 |
| trans heptene-2 | 0.377 | 0.183 | 0.194 |
| cis heptene-2 | 0.202 | 0.035 | 0.167 |

Separation factor*
Normal over branched olefins: 31
Cis-heptene-2 over 5-methylhexene-2: 3.7

EXAMPLE III

The conditions of Example I were again repeated. The separation factor of normal over branched olefins was determined. The data are in Table III.

TABLE III

| | |
|---|---|
| Pretreatment temperature of 5A molecular sieves | 700° F. |
| Experimental temperature | 79° F. |
| Adsorbent charged | 10.215 grams |
| Feed charged | 6.557 grams |

Composition of liquids, gram/gram of 2,4 dimethylpentane

| | Feed | Adsorbed | Raffinate |
|---|---|---|---|
| 2,4 dimethylpentane | 1.0 | | 1.0 |
| 2,4-dimethylpentene-1 | 0.688 | 0.265 | 0.423 |
| 2,4-dimethylpentene-2 | | | |
| 2-methylhexene-1 | 0.629 | 0.351 | 0.278 |
| 2-methylhexene-2 | | | |
| trans heptene-2 | 0.577 | 0.447 | 0.130 |
| cis heptene-2 | 0.328 | 0.125 | 0.203 |

Separation factor:
Normal over branched olefins: 2.0

The 5A molecular sieves pretreated at a temperature higher than 500° F. as shown in Tables II and III, cannot give a high degree of separation between a normal cis-olefin (cis-heptene-2) and branched olefins. In Table I, 5A molecular sieves pretreated at 400°–500° F. give a satisfactory separation between a normal cis-olefin (cis-heptene-2) and branched olefins.

Table II illustrates that 5A molecular sieves, when pretreated at 700° F., give a separation factor for cis-heptene-2 over 5-methylhexene-2 of only 3.7 although the overall normal-over-branched olefin separation factor can be as high as 31. Thus, normal cis-olefins cannot be recovered to a great degree along with other normal olefins if the pretreatment temperature is over 500° F.

Accordingly, the overall selectivity for normal over branched olefins can become poor when a hydrocarbon mixture contains a relatively large amount of normal cis-olefins and branch-chained olefins such as olefins in the form of

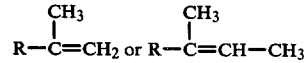

which are branched. With 5A molecular sieves pretreated at 700° F., as illustrated in Table III, the normal olefins were extracted with a separation factor of only 2.0 with a mixture containing cis-heptene-2, and the branched compounds of 2-methylhexene-1 and 2-methylhexene-2. Consequently, 5A molecular sieves pretreated at a temperature higher than 500° F. are not satisfactory for normal olefin recovery. Satisfactory normal olefin recovery was achieved with 5A molecular sieves when the molecular sieves were pretreated at 400°–500° F., achieving a separation factor of 30.

What is claimed is:

1. A process for increasing the concentration of normal cis olefins in a hydrocarbon composition, which comprises passing a hydrocarbon composition comprising normal cis olefins containing from about 4 to 20 carbon atoms and at least one member selected from the group consisting of branched olefins containing from about 4 to 20 carbon atoms, branched and normal paraffins containing from about 4 to 20 carbon atoms and aromatic hydrocarbons into a pretreated molecular sieve adsorption zone, withdrawing unadsorbed hydrocarbons and recovering adsorbed hydrocarbons having said increased concentration of normal cis isomers wherein said molecular sieve has been pretreated with water vapor for a period of 1 to 6 hours within the range from about 400° to about 500° F. to reach the stable water-zeolite equilibrium at said temperature range in the presence of water.

2. The process of claim 1 wherein the feed stream is selected from the group of hydrocarbon feedstocks consisting of a 190°–310° F. heavy catalytic naphtha fraction containing $C_7$–$C_9$ normal olefins composed of $C_4$ to $C_{12}+$ olefins of an API gravity of 57.4 and a coker naphtha having a boiling point within the range of from 60° to 420° F.

3. The process of claim 1 wherein the said molecular sieve zeolite is selected from the group consisting of chabazite, mordenite, gmelinite, erionate, zeolite A, zeolite D, zeolite R, zeolite S and zeolite T.

4. The process of claim 1 wherein the said zeolite is zeolite 5A.

5. The process of claim 1 wherein the feed stream consists essentially of 4 to 10 carbon atoms per molecule.

6. The process of claim 1 wherein the feed stream consists essentially of 6 to 9 carbon atoms per molecule.

7. The process of claim 1 wherein the adsorption occurs in gas phase.

8. The process of claim 1 wherein the adsorption occurs in liquid phase.

UNITED STATES PATENT OFFICE
CERTIFICATE OF CORRECTION

Patent No. 4,186,082            Dated January 29, 1980

Inventor(s) Chi-Hung Lin and William F. Pansing, deceased, by
Evelyn Pansing Boyle, legal representative It is certified that error appears in the above-identified patent and that said Letters Patent are hereby corrected as shown below:

Patent
| Column | Line | |
|---|---|---|
| 1 | 12 | "alchols" should be --alcohols-- |
| 1 | 57 | "Izu" should be --Izv-- |
| 4 | 65 | "surprisingly" should be --surprising-- |

Signed and Sealed this

Seventeenth Day of June 1980

[SEAL]

*Attest:*

*Attesting Officer*

SIDNEY A. DIAMOND

*Commissioner of Patents and Trademarks*